United States Patent [19]

Andors

[11] Patent Number: 4,898,590

[45] Date of Patent: Feb. 6, 1990

[54] SYRINGE HAVING PROTECTIVE SLEEVE

[75] Inventor: Leonard Andors, Brookhaven, N.Y.

[73] Assignee: Research Foundation of the State University of N.Y., Albany, N.Y.

[21] Appl. No.: 211,476

[22] Filed: Jun. 24, 1988

[51] Int. Cl.$^4$ .............................................. A61M 5/32
[52] U.S. Cl. .................................... 604/198; 604/263
[58] Field of Search ............... 604/192, 197, 198, 263, 604/110

[56] References Cited

U.S. PATENT DOCUMENTS

| | | | |
|---|---|---|---|
| 788,935 | 5/1905 | McKinley et al. | 604/197 |
| 2,571,653 | 10/1951 | Bastien . | |
| 2,876,770 | 3/1959 | White | 604/198 |
| 2,925,083 | 2/1960 | Craig | 604/197 |
| 3,046,985 | 7/1962 | Scenz | 604/197 |
| 3,134,380 | 5/1964 | Armao . | |
| 3,884,230 | 5/1975 | Wulff . | |
| 3,890,971 | 6/1975 | Leeson et al. . | |
| 4,373,526 | 2/1983 | Kling . | |
| 4,425,120 | 1/1984 | Sampson et al. . | |
| 4,573,976 | 3/1986 | Sampson et al. . | |
| 4,631,057 | 12/1986 | Mitchell . | |
| 4,655,751 | 4/1987 | Harbaugh . | |
| 4,664,653 | 5/1987 | Sagstetter et al. . | |
| 4,664,654 | 5/1987 | Strauss . | |
| 4,675,005 | 6/1987 | DeLuccia . | |
| 4,681,567 | 7/1987 | Masters et al. . | |
| 4,693,708 | 9/1987 | Wanderer et al. . | |
| 4,702,738 | 10/1987 | Spencer . | |
| 4,702,739 | 10/1987 | Milorad . | |
| 4,723,943 | 2/1988 | Spencer . | |
| 4,725,267 | 2/1988 | Vaillancourt . | |
| 4,737,144 | 4/1988 | Choksi . | |
| 4,738,663 | 4/1988 | Bogan . | |
| 4,772,272 | 9/1988 | McFarland | 604/198 |

Primary Examiner—C. Fred Rosenbaum
Assistant Examiner—Mark O. Polutta
Attorney, Agent, or Firm—Hoffmann & Baron

[57] ABSTRACT

A syringe is provided which includes a sleeve for protecting against accidental needle stick. The syringe includes a cylindrical barrel including a pair of opposing openings, one of which is elongate to allow a cartridge to be loaded or removed therethrough. The sleeve includes a pair of corresponding openings which are registrable with the barrel openings when the sleeve is in the retracted position. The sleeve accordingly does not interfere with the normal cartridge loading and removal procedures. Once an injection has been completed, the sleeve may be moved to the extended position and the syringe needle can be safety recapped.

13 Claims, 1 Drawing Sheet

U.S. Patent  Feb. 6, 1990  4,898,590
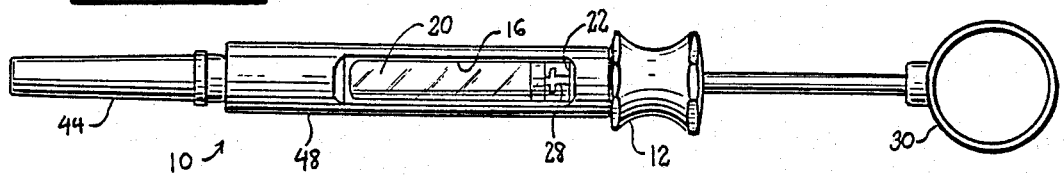
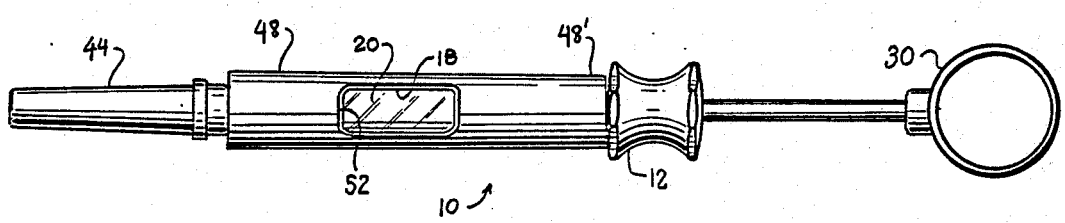
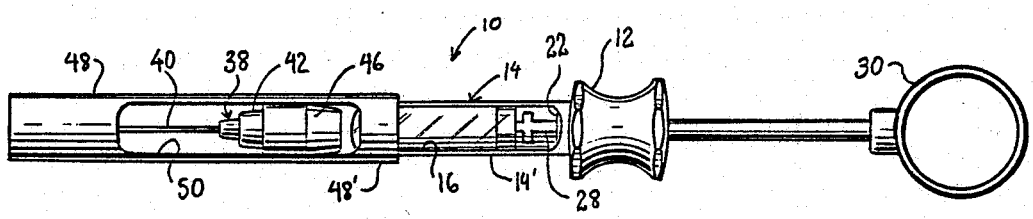
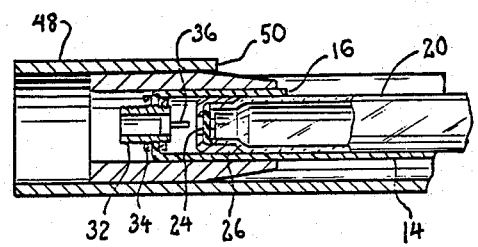
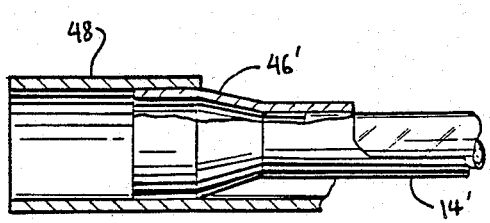

SYRINGE HAVING PROTECTIVE SLEEVE

BACKGROUND OF THE INVENTION

The invention relates to a syringe having a protective sleeve for preventing injury and possible disease caused by accidental contact with a needle mounted to the syringe.

Syringes are commonly used for the administration of medicinal liquids, anesthetics and other substances. In view of the possibility that the patient receiving an injection may be suffering from an infectious disease, it is extremely important to insure that the needle used for such injection does not subsequently wound another person.

Hypodermic needles and syringes are usually prepackaged with a shield which protects the needle and the user prior to administration of the substance to be injected. While the shield provides adequate protection prior to injection, disposal of the needle subsequent thereto has posed significant risks for doctors, nurses and other personnel. Reinstallation of the shield presents the greatest risk as improper centering of the needle with respect thereto can easily result in the sticking of one of the fingers holding the shield. Gloves do not provide adequate protection against such accidents. Recent studies have indicated that as many as 800,000 accidental needle sticks occur within each twelve month period.

Various attempts have been made to minimize the possibility of injury from hypodermic needles and the like. For example, U.S. Pat. No. 4,702,738 discloses the use of a sheath which is slidably mounted to a syringe barred and is irreversibly locked in a position covering the needle after the syringe has been used. U.S. Pat. No. 4,738,663 discloses a hypodermic syringe having a sleeve which is slidably mounted to the syringe barrel and movable between extended and retracted positions.

Certain types of syringes, such as dental anesthetic syringes, are relatively expensive and accordingly are not discarded after being used to inject a patient. The needles used in connection therewith are, of course, discarded once the patient has been anesthetized, but the syringe itself is sterilized in an autoclave.

Such local anesthetic syringes provided by most major manufacturers include a housing containing a first spring-loaded plunger, a cylindrical enclosure extending from the housing and having one or more elongate openings therein and an internally threaded opening at one end thereof, and a second plunger extending through the first plunger. The second plunger includes a handle member secured to one end thereof. A cylindrical cartridge may be loaded into the enclosure by withdrawing the spring-loaded plunger into the housing and inserting the cartridge through the elongate opening. A double-ended needle assembly is mounted to the internally threaded end of the enclosure prior to loading the cartridge. One end of this needle assembly accordingly pierces the cartridge once the spring-loaded plunger is released. The other end of the needle is protected by a sheath until the syringe is used.

Once the patent has been sufficiently anesthetized, the sheath is again mounted to the needle assembly, a procedure which entails the same risks as those associated with other syringes. The cartridge is removed by withdrawing, the spring-loaded plunger and pushing it through the elongate opening in the cylindrical enclosure.

The usual construction of non-disposable syringes having removable cartridges does not lend itself to the application of conventional protective sleeves and sheaths, which would preclude access to the cartridge whether in extended or withdrawn positions. In addition, none of these protective sleeve assemblies are readily adaptable for use on existing syringes which are not originally equipped to use such assemblies.

SUMMARY OF THE INVENTION

In view of the ever-increasing need to protect against accidental injury from used hypodermic needles and the like, it is an object of the invention to provide a syringe having a protective sleeve which can be moved between extended and retracted positions wherein a needle mounted to the syringe can be covered or exposed.

It is another object of the invention to provide a protective sleeve for a syringe which will allow a disposable cartridge to be inserted or removed from an enclosure therefor without the need for removing the protective sleeve.

A still further object of the invention is to provide a protective sleeve assembly which can be retroactively fitted to a syringe having an enclosure for a removable cartridge and which will not interfere with either the operation of the syringe or the removability of the cartridge.

In accordance with these and other objectives, a syringe is provided which comprises a housing including a barrel extending therefrom, the syringe barrel including an elongate opening through which a cartridge may be inserted or removed, a protective sleeve slidably mounted to the barrel, the sleeve being movable between extended and retracted positions to cover or expose a needle projecting from an end of the barrel, the sleeve being movable to a position wherein the elongate opening within the barrel is sufficiently accessible to allow insertion or removal of a cartridge therethrough. The sleeve preferably includes an elongate opening which can be positioned in registry with the opening within the syringe barrel to facilitate loading or removing the cartridge.

The syringe barrel preferably includes a second opening in opposing relation to the elongate opening to allow the user to push the cartridge through the elongate opening. The sleeve preferably also includes a second opening which can be positioned in registry with the second opening within the syringe barrel.

Retaining means are provided near the distal end of the syringe barrel to prevent the sleeve from being inadvertently removed from the barrel. The retaining means may be defined by an integral ring or flange defined by the syringe barrel or a separate retaining structure which is secured thereto. The latter structure is necessary where the sleeve is to be retrofitted to conventional syringes.

BRIEF DESCRIPTION OF THE DRAWINGS

FIG. 1 is a top plan view of syringe in accordance with the invention;

FIG. 2 is a bottom plan view thereof;

FIG. 3 is a top plan view thereof showing a protective sleeve in an extended position;

FIG. 4 is a sectional view thereof taken along line 4—4 in FIG. 1; and

FIG. 5 is a sectional view of a second embodiment of the invention including a protruding ring defined by an end of the syringe barrel.

DETAILED DESCRIPTION OF THE INVENTION

A dental anesthetic syringe 10 is shown in FIGS. 1-4. The syringe includes a spool-shaped housing 12 having a substantially cylindrical barrel 14 extending therefrom and a passage extending therethrough.

The barrel includes a first elongate opening 16 extending through the walls 14' thereof as shown in FIG. 1 and a second, smaller opening 18 as shown in FIG. 2. The two barrel openings within the longitudinal walls thereof are in opposing relation to each other.

A cartridge 20 is positioned within a chamber defined by the syringe barrel and is resiliently urged towards one end thereof by a spring-loaded plunger 22 extending from the passage within the housing 12. The cartridge includes a resilient, polymeric piston positioned therein which seals one end thereof. The opposite end is sealed by a resilient diaphragm 24 which is maintained in a fixed position by an end cap 26.

A second plunger 28 is mounted to the syringe housing 12 and extends through the spring-loaded plunger 22. A handle 30 is mounted to one end of this plunger. A peripheral flange is defined near the opposite end thereof which bears against the spring-loaded plunger 22 when the second plunger is completely retracted. By increasing the distance between the housing 12 and the handle 30, the spring-loaded plunger 22 is withdrawn into the housing 12 due to the pressure exerted thereon by the peripheral flange. The cartridge 20 may be loaded or removed while the plunger 22 is in the retracted position.

As shown in FIGS. 3 and 4, the syringe barrel 14 includes an opening at one end thereof which is aligned with the diaphragm 24 of the cartridge 20. An externally threaded cylindrical projection 32 extends outwardly from the barrel and a resilient washer 34 is mounted to this projection. An internally extending projection 36 is positioned in alignment with the cartridge diaphragm 24.

A double-ended needle assembly 38 is threadably secured to the outwardly extending projection 32. One end of the needle 40 penetrates the diaphragm 24 of the cartridge while the other end extends outwardly from the syringe. A plastic, internally threaded needle assembly housing 42 bears against the washer 34 to prevent leakage. A sheath 44 is mounted to the housing and protects the needle when not in use. It also allows the user to safely install or remove the needle by turning it in the appropriate direction with respect to the threaded cylindrical projection 32.

A tapered ring 46 is secured near an end of the syringe barrel. A substantially cylindrical sleeve 48 is slidably mounted to the cylindrical portion of the ring 46. The inner diameter of one end portion 48' of the sleeve is smaller than that of the remainder of the sleeve. When the sleeve is moved a sufficient distance from the syringe housing 12, this end portion 48' abuts the ring and prevents the sleeve from being disassociated from the syringe.

A pair of openings 50,52 are provided within the side walls of the sleeve 48. The first opening 50 is sufficient in length and width to allow the cartridge 20 to be inserted therethrough. The second opening 52 is located in opposing relation with respect to the first opening and is of sufficient size to allow the user's finger to be at least partially inserted therein.

When fully extended, the sleeve extends far enough beyond the point of the needle that a user would be extremely unlikely to stick his finger thereon. The walls of the sleeve aid the user in guiding the protective sheath 44 into position over the needle 40.

As shown in a second embodiment of the invention illustrated in FIG. 5, the retaining ring may be an integrally formed annular protrusion 46' extending radially from the syringe barrel 14'. The other parts of the syringe would remain essentially the same.

In operation, a dentist or other suitably trained person would remove the syringe 10 from a sterilizing apparatus (not shown) prior to loading the cartridge and securing the double-ended needle assembly 38. The sleeve 48 is pushed towards the housing 12 until it abuts the upper surface thereof. It is then rotated about its longitudinal axis until the openings 50, 52 therein are in alignment with the corresponding openings 16,18 in the syringe barrel 14. As the spring-loaded plunger 22 is withdrawn into the housing 12 by urging the handle 30 away from the housing, the cartridge 20 is inserted through the openings 50,16 and into the barrel. By releasing the handle 30, the cartridge will be maintained in position by the force of the plunger 22 which resiliently urges it against the front end portion of the barrel.

The double-ended needle assembly 38 is provided in a sterilized container (not shown) to protect it from contamination. The inner end of the needle 40 is inserted within the opening at one end of the barrel until the housing 42 is positioned over the externally threaded projection 32. It is then rotated about its longitudinal axis by turning the sheath 44 in the clockwise direction, thereby securing the assembly to the projection 32. The inner end of the needle passes through the internally extending barrel projection 36 and pierces the cartridge diaphragm 24. Upon removal of the sheath 44, the syringe is ready for use.

To remove the cartridge, the elongate openings 50, 16 are again aligned by rotating the sleeve with respect to the barrel. The spring-loaded plunger 22 is withdrawn into the syringe housing 12. The cartridge may then be moved towards the housing and pushed through the elongate openings 16,50 by inserting a finger through the second set of openings 18,52.

Once the final injection has been made, the sleeve 48 is moved away from the housing 12 and into abutment with the retaining ring 46. The needle 40 is thereby covered by the sleeve to prevent accidental needle stick. The point of the needle preferably extends beyond either sleeve opening 50,52, as shown in FIG. 3, but not as far as the outer end of the sleeve. The needle may be safely recapped with the sheath 44 while the sleeve is in the extended position. After recapping, the sleeve is moved back into contact with the housing 12 and the needle assembly 38, including the sheath 44, is unscrewed from the syringe.

While frictional contact between the retaining ring 46 and the sleeve 48 is sufficient to maintain the sleeve in any desired longitudinal or rotational position, means may be provided for locking the sleeve in the extended position. Such locking means may include, for example, an annular recess formed within the retaining ring. The sleeve may include a corresponding internal rib which snaps within the recess. A second such rib may be provided near the opposite end of the sleeve for locking the sleeve in the position adjacent the housing 12. Means may also be provided for insuring the sleeve openings are always properly aligned with the corresponding barrel openings.

A safe and economical solution to the problem of accidental needle stick is accordingly provided by the invention. The invention provides means for retrofitting a protective sleeve to existing syringes, as shown in FIGS. 1-4, as well as a simple construction as shown in FIG. 5 for newly manufactured syringes. While described in terms of dental anesthetic syringes, the invention would have application to any syringes including means for housing replaceable cartridges.

What is claimed is:

1. A syringe comprising:
   a barrel including longitudinal walls defining an elongate chamber therein for receiving a cartridge;
   a first, elongate opening defined within said longitudinal walls through which a cartridge may be inserted into said chamber;
   a second opening defined within said longitudinal walls of said barrel, said second opening in opposing relation to said first, elongate opening;
   a sleeve slidably mounted to said barrel, said sleeve including a first, elongate opening and a second opening, said second sleeve opening being in opposing relation to said first, elongate sleeve opening, said sleeve being movable to a position with respect to said barrel such that said first and second sleeve openings are substantially in register with said first and second barrel openings; and
   means for retaining said sleeve upon said barrel.

2. A syringe as defined in claim 1 wherein said retaining means includes a ring secured to said barrel.

3. A syringe as defined in claim 2 wherein said sleeve is slidably mounted to said ring.

4. A syringe as defined in claim 3 wherein said ring includes a cylindrical portion and a frustoconical portion extending from said cylindrical portion, said sleeve being mounted to said cylindrical portion of said ring.

5. A syringe as defined in claim 1 wherein said retaining means is an annular protrusion integral with said barrel.

6. A syringe defined in claim 1 wherein said sleeve is rotatable with respect to said barrel.

7. A syringe as defined in claim 1 including a syringe housing, said barrel being secured to an extending from said syringe housing, said sleeve being abuttable against said syringe housing.

8. A syringe as defined in claim 7 wherein said first and second sleeve openings are registrable with said first and second barrel openings, respectively, when said sleeve is in adjoining relation with respect to said syringe housing.

9. A syringe as defined in claim 8 wherein said barrel and said sleeve are each substantially cylindrical in configuration.

10. A syringe as defined in claim 8 including a double ended needle assembly mounted to said barrel.

11. A syringe as defined in claim 10 wherein said retaining means is secured to said barrel and in opposing relation to said syringe housing.

12. A syringe as defined in claim. 11 wherein said sleeve includes means for abutting said retaining means, said needle assembly being completely enclosed by said sleeve when said sleeve is in abutting relation with said retaining means.

13. A syringe as defined in claim 1 wherein said retaining means is a ring including a cylindrical portion having a frustoconical portion extending therefrom, said sleeve being slidably mounted to said cylindrical portion of said ring.

* * * * *